(12) United States Patent
Bates

(10) Patent No.: US 6,800,080 B1
(45) Date of Patent: Oct. 5, 2004

(54) MEDICAL RETRIEVAL DEVICE

(75) Inventor: James S. Bates, Bloomington, IN (US)

(73) Assignee: SCIMED Life Systems, Inc., Maple Grove, MN (US)

(*) Notice: Subject to any disclaimer, the term of this patent is extended or adjusted under 35 U.S.C. 154(b) by 0 days.

(21) Appl. No.: 09/588,373

(22) Filed: Dec. 22, 1999

Related U.S. Application Data

(63) Continuation of application No. 09/084,135, filed on May 22, 1998, now Pat. No. 6,096,053, which is a continuation-in-part of application No. 08/642,756, filed on May 3, 1996, now Pat. No. 5,935,139.

(51) Int. Cl.[7] ............................................. A61B 17/22
(52) U.S. Cl. ..................................... 606/127; 606/200
(58) Field of Search ............................ 606/1, 113, 106, 606/127, 128, 114, 159, 110; 604/96.01

(56) References Cited

U.S. PATENT DOCUMENTS

| | | | |
|---|---|---|---|
| 2,556,783 A | 6/1951 | Wallace | 128/321 |
| 2,943,626 A | * 7/1960 | Dormia | 606/127 |
| 3,137,298 A | 6/1964 | Glassman | 128/328 |
| 3,472,230 A | 10/1969 | Fogarty | |
| 3,828,790 A | 8/1974 | Curtiss et al. | 128/320 |
| 3,955,578 A | 5/1976 | Chamness et al. | 128/303.15 |
| 3,996,938 A | 12/1976 | Clark, III | 128/348 |
| 4,046,150 A | 9/1977 | Schwartz et al. | 128/328 |
| 4,198,960 A | 4/1980 | Utsugi | 128/6 |
| 4,243,040 A | 1/1981 | Beecher | 128/328 |

(List continued on next page.)

FOREIGN PATENT DOCUMENTS

| | | |
|---|---|---|
| AU | 56865/86 | 4/1986 |
| DE | 2804058 | 8/1978 |
| DE | 2821048 | 11/1979 |
| DE | 3213223 A1 | 10/1983 |
| DE | 3407708 A1 | 9/1985 |
| DE | 3522649 A1 | 1/1986 |
| DE | 3620385 C1 | 1/1988 |
| DE | 3633527 A1 | 4/1988 |
| DE | 4025799 A1 | 2/1992 |
| DE | 32 13 223 A1 | 10/1993 |

(List continued on next page.)

OTHER PUBLICATIONS

Vorwerk, Dierk et al., "Percutaneous Embolectomy: In Vitro Investigations of the Self–expanding Tulip Sheath", *Radiology* (1992) 182: 415–418.

Vorwerk, Dierk et al., "Percutaneous Balloon Embolectomy with a Self–expanding Tulip Sheath: In Vitro Experiments", *Radiology* (1995) 197: 153–156.

Moussa et al., "Stents Don't Require Systemic Anticoagulation . . . But the Technique (and Results) Must be Optimal," *The Journal of Invasive Cardiology*, vol. 8, Suppl. E, 1996, pp. 3E–30E, Health Management Productions, Inc.

*Primary Examiner*—Kevin Truong
(74) *Attorney, Agent, or Firm*—Finnegan, Henderson, Farabow, Garrett & Dunner, L.L.P.

(57) ABSTRACT

Immobilization and/or retrieval of material from a body can be accomplished, in accordance with the invention, with a device that includes a sheath and a basket. The basket is movable relative to the sheath from a retracted position in which the basket is withdrawn within the sheath and an expanded position in which the basket is extended beyond the distal end of the sheath and open. The basket has a first portion and a second portion with two or more legs extending from the first portion to the second portion. The basket further includes an intermediate portion between the first and second portions in which the legs are spirally arranged, substantially parallel, and non-intersecting. The intermediate portion of the basket is displaced radially outward relative to the first and second portions when the basket is in the expanded position. The basket in the expanded position may be used to immobilize and/or capture material within a body.

17 Claims, 13 Drawing Sheets

U.S. PATENT DOCUMENTS

| | | | |
|---|---|---|---|
| 4,299,225 A | 11/1981 | Glassman | 128/328 |
| 4,326,530 A | 4/1982 | Fleury, Jr. | 128/303.14 |
| 4,347,846 A | 9/1982 | Dormia | 128/328 |
| 4,425,908 A | 1/1984 | Simon | 128/1 R |
| 4,447,227 A | 5/1984 | Kotsanis | 604/95 |
| 4,557,255 A | 12/1985 | Goodman | 128/7 |
| 4,590,938 A | 5/1986 | Segura et al. | 128/328 |
| 4,611,594 A | 9/1986 | Grayhack et al. | 128/328 |
| 4,612,931 A | 9/1986 | Dormia | 128/328 |
| 4,625,726 A | 12/1986 | Duthoy | 128/328 |
| 4,650,466 A | 3/1987 | Luther | 604/95 |
| 4,682,599 A | 7/1987 | Konomura | 128/328 |
| 4,691,705 A | 9/1987 | Okada | 128/328 |
| 4,699,147 A | 10/1987 | Chilson et al. | 128/642 |
| 4,706,671 A | 11/1987 | Weinrib | 128/348.1 |
| 4,718,419 A | 1/1988 | Okada | 128/303.15 |
| 4,723,549 A | 2/1988 | Wholey et al. | 128/344 |
| 4,728,319 A | 3/1988 | Masch | 604/22 |
| 4,790,812 A | 12/1988 | Hawkins, Jr. et al. | 604/22 |
| 4,790,813 A | 12/1988 | Kensey | 604/22 |
| 4,794,928 A | 1/1989 | Kletschka | 128/344 |
| 4,807,626 A | 2/1989 | McGirr | 128/328 |
| 4,873,978 A | 10/1989 | Ginsburg | 128/345 |
| 4,885,003 A | 12/1989 | Hillstead | 604/22 |
| 4,893,621 A | 1/1990 | Heyman | 606/127 |
| 4,907,572 A | 3/1990 | Borodulin et al. | 606/128 |
| 4,926,858 A | 5/1990 | Gifford, III et al. | 606/159 |
| 4,927,426 A | 5/1990 | Dretler | 606/128 |
| 4,927,427 A | 5/1990 | Kriauciunas et al. | 606/128 |
| 4,960,108 A * | 10/1990 | Reichel et al. | 601/4 |
| 4,994,079 A | 2/1991 | Genese et al. | 606/206 |
| 4,997,435 A * | 3/1991 | Demeter | 604/104 |
| 4,998,539 A | 3/1991 | Delsanti | 128/898 |
| 5,011,488 A | 4/1991 | Ginsburg | 606/159 |
| 5,030,201 A | 7/1991 | Palestrant | 604/22 |
| 5,041,093 A | 8/1991 | Chu | 604/104 |
| 5,053,008 A | 10/1991 | Bajaj | 604/104 |
| 5,057,114 A | 10/1991 | Wittich et al. | 606/127 |
| 5,064,428 A | 11/1991 | Cope et al. | 606/127 |
| 5,071,407 A | 12/1991 | Termin et al. | 604/104 |
| 5,084,054 A | 1/1992 | Bencini et al. | 606/113 |
| 5,100,423 A | 3/1992 | Fearnot | 606/159 |
| 5,102,415 A | 4/1992 | Guenther et al. | 604/159 |
| 5,171,233 A | 12/1992 | Amplatz et al. | 604/281 |
| 5,176,688 A | 1/1993 | Narayan et al. | 606/128 |
| 5,192,286 A | 3/1993 | Phan et al. | 606/127 |
| 5,246,447 A * | 9/1993 | Rosen et al. | 601/24 |
| 5,290,294 A | 3/1994 | Cox et al. | 606/108 |
| 5,311,858 A | 5/1994 | Adair | 128/4 |
| 5,329,942 A | 7/1994 | Gunther et al. | 128/898 |
| 5,330,482 A | 7/1994 | Gibbs et al. | 606/113 |
| 5,345,936 A | 9/1994 | Pomeranz et al. | 128/642 |
| 5,354,310 A | 10/1994 | Garnic et al. | 606/198 |
| 5,376,100 A | 12/1994 | Lefebvre | 606/180 |
| 5,380,273 A | 1/1995 | Dubrul et al. | 604/22 |
| 5,421,832 A | 6/1995 | Lefebvre | 604/53 |
| 5,441,516 A | 8/1995 | Wang et al. | 606/198 |
| 5,496,330 A | 3/1996 | Bates et al. | 606/127 |
| 5,499,981 A | 3/1996 | Kordis | 606/41 |
| 5,549,626 A | 8/1996 | Miller et al. | 606/200 |
| 5,562,678 A * | 10/1996 | Booker | 606/106 |
| 5,658,296 A | 8/1997 | Bates et al. | 606/127 |
| 5,693,069 A * | 12/1997 | Shallman | 606/110 |
| 5,713,848 A | 2/1998 | Dubrul et al. | 604/22 |
| 5,814,064 A | 9/1998 | Daniel et al. | 606/200 |
| 5,928,260 A * | 7/1999 | Chin et al. | 606/200 |
| 5,935,139 A | 8/1999 | Bates | 606/159 |
| 6,096,053 A | 8/2000 | Bates | 606/159 |
| 6,174,318 B1 * | 1/2001 | Bates et al. | 606/113 |
| 6,248,113 B1 * | 6/2001 | Fina | 606/127 |
| 6,277,084 B1 * | 8/2001 | Abele et al. | 29/270 |

FOREIGN PATENT DOCUMENTS

| | | |
|---|---|---|
| EP | 0 195 444 | 9/1986 |
| EP | 0 428 998 A1 | 5/1991 |
| EP | 0 737 450 A1 | 10/1996 |
| GB | 2 020 557 A | 11/1979 |
| GB | 2271932 | 5/1994 |
| JP | 3-205043 | 9/1991 |
| WO | 91/11209 | 8/1991 |
| WO | 92/05828 | 4/1992 |
| WO | 92/16153 | 10/1992 |
| WO | 94/24946 | 11/1994 |
| WO | 95/05129 | 2/1995 |
| WO | 96/01591 | 1/1996 |
| WO | 96/23446 | 8/1996 |
| WO | 97/27808 | 8/1997 |
| WO | 97/41782 | 11/1997 |

* cited by examiner

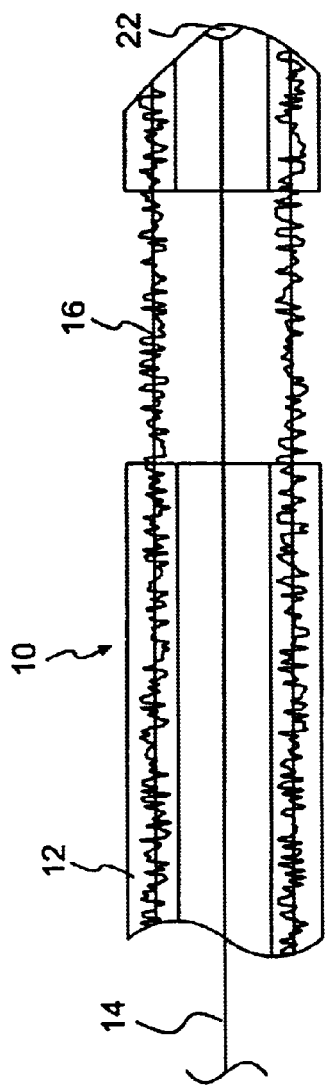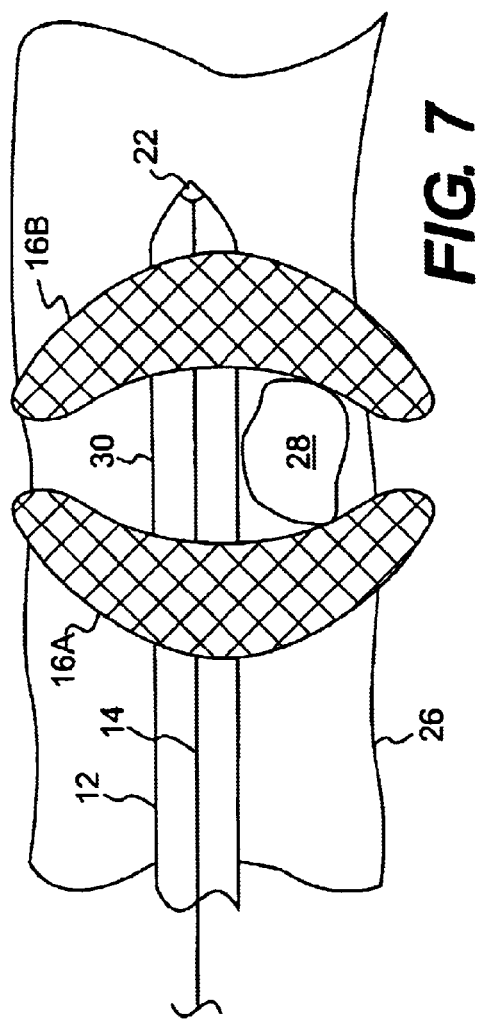

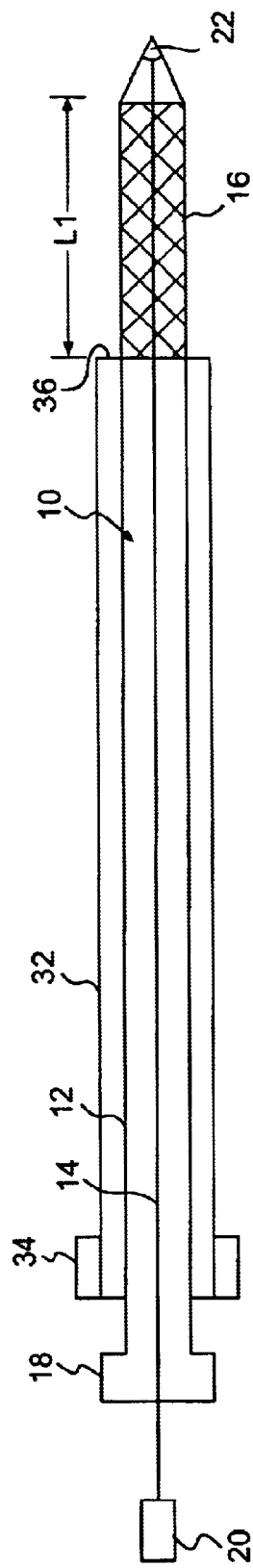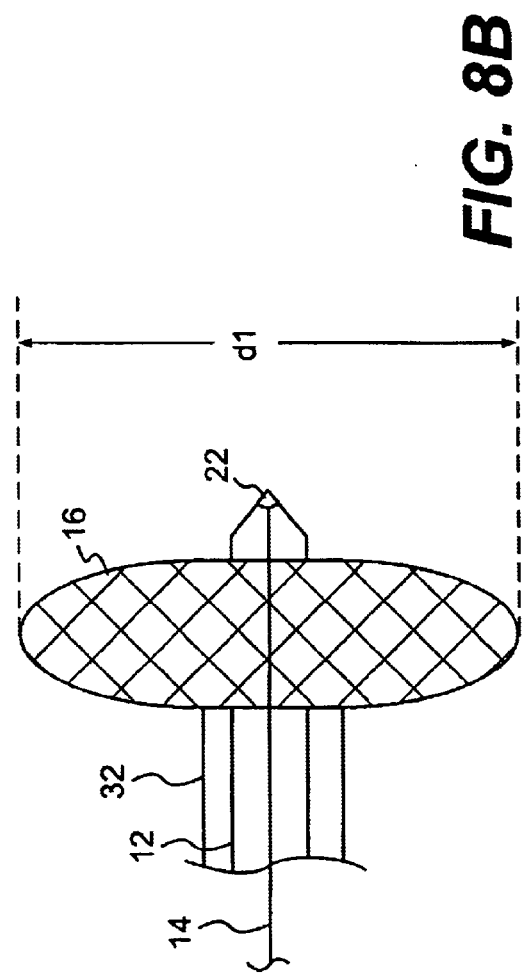

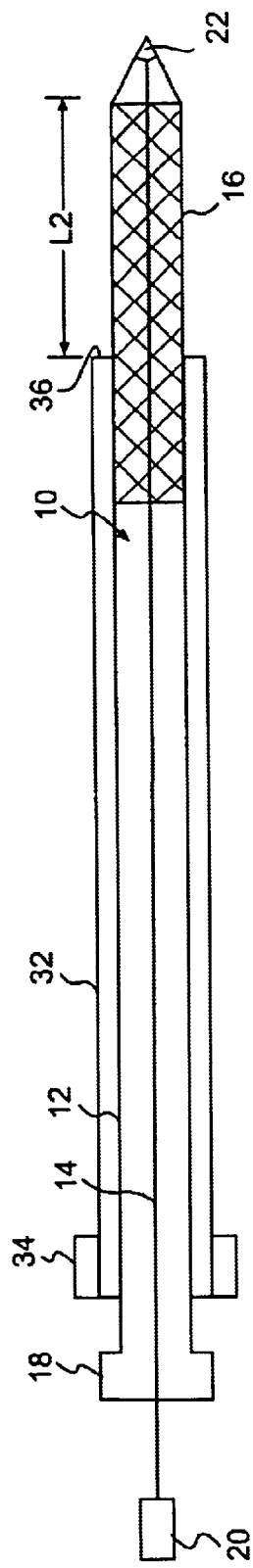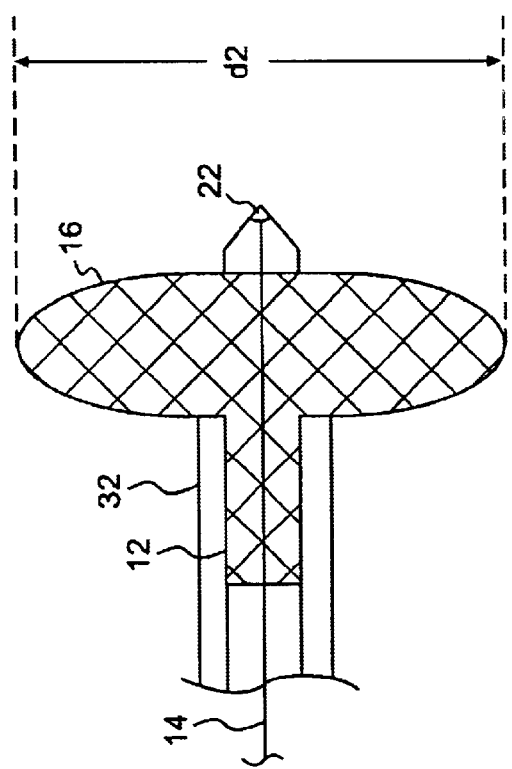

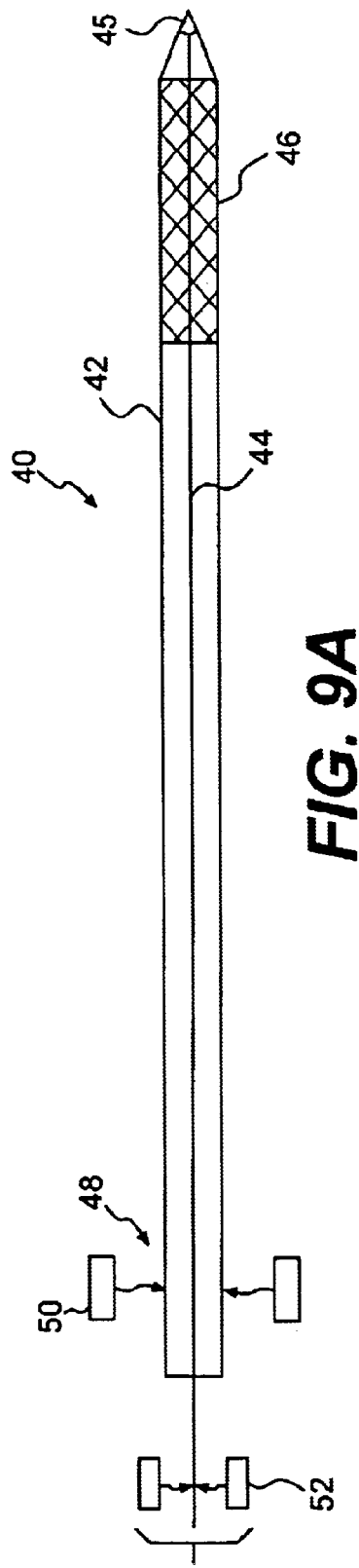
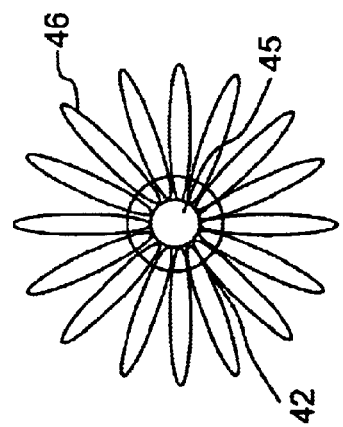
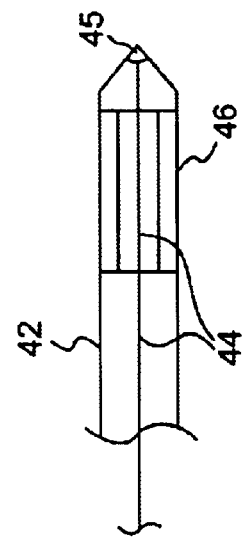
FIG. 9A
FIG. 9B
FIG. 9C

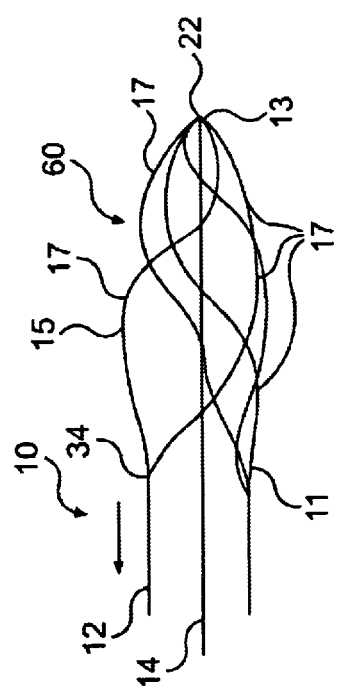
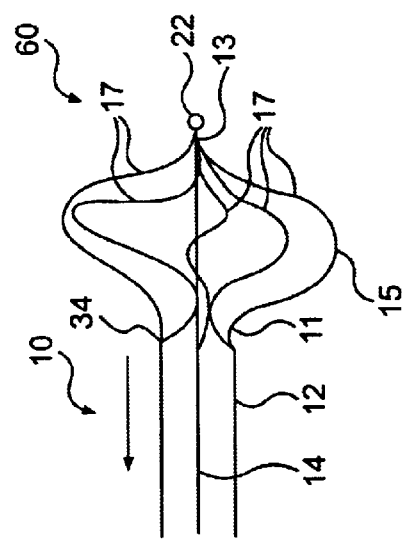
FIG. 11A
FIG. 11B

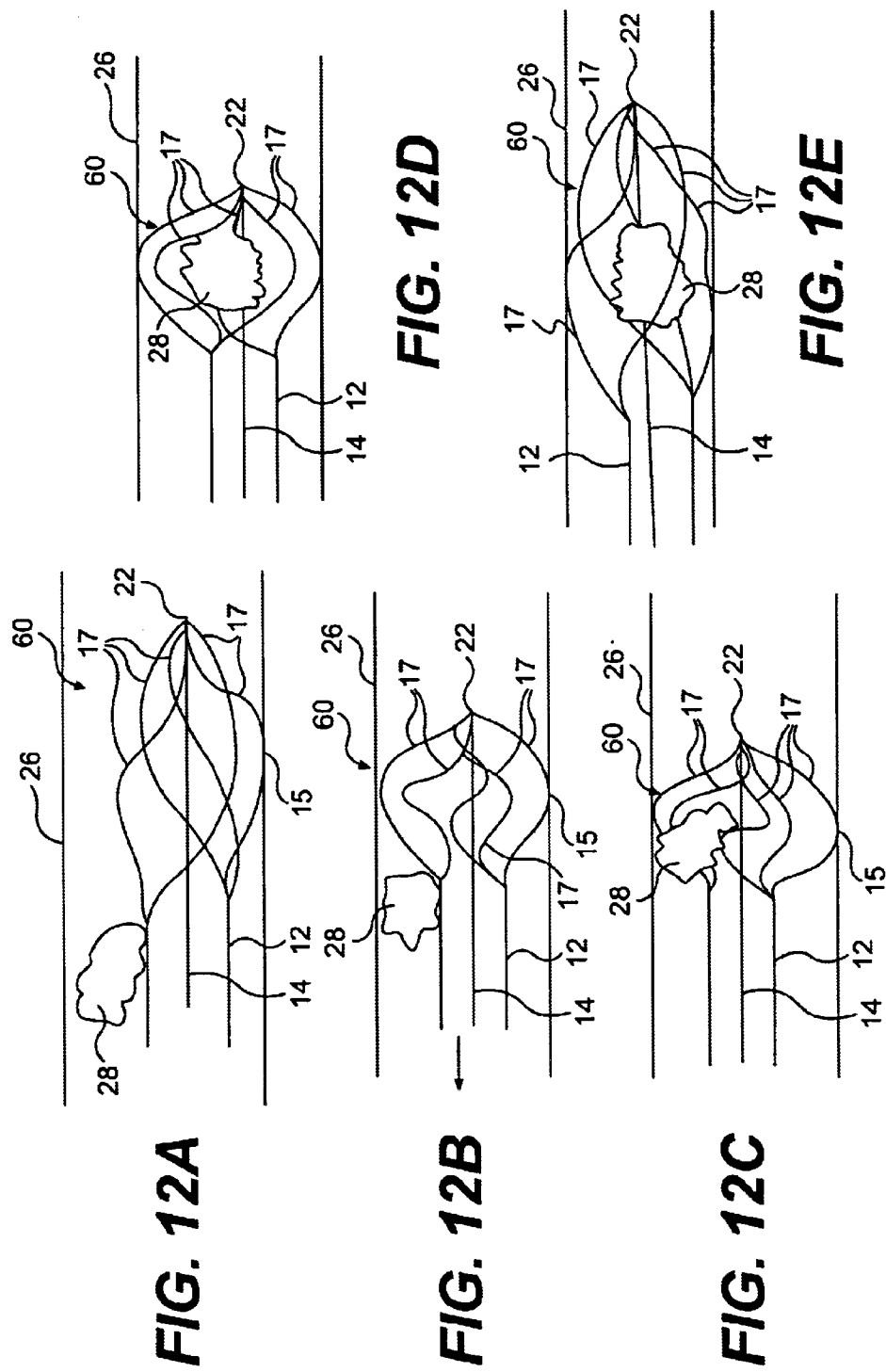

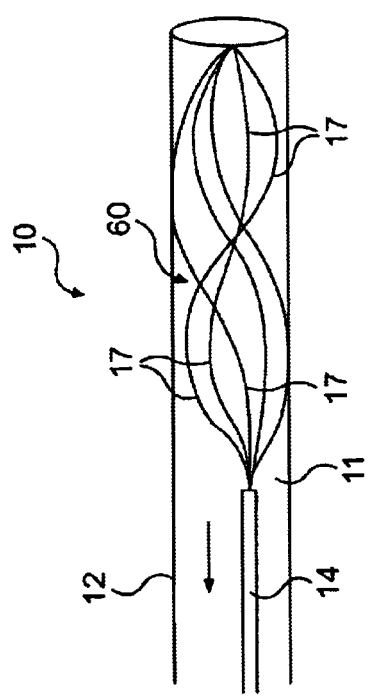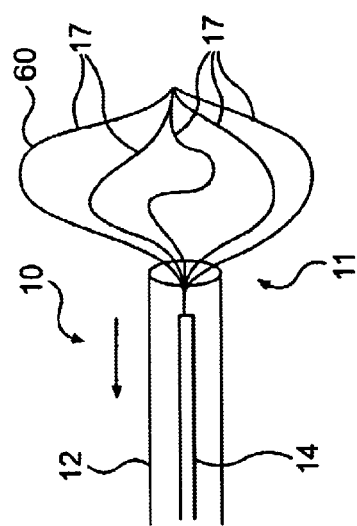

MEDICAL RETRIEVAL DEVICE

CROSS-REFERENCE TO RELATED CASES

This is a continuation of U.S. patent application Ser. No. 09/084,135 filed May 22, 1998, now issued as U.S. Pat. No. 6,096,053, which is continuation-in-part of U.S. patent application Ser. No. 8/642,756 filed on May 3, 1996, now issued as U.S. Pat. No. 5,935,139. Also U.S. Pat No. 5,160,336 is incorporated herein by reference.

TECHNICAL FIELD

The present invention deals with a retrieval device for removing material from a body.

BACKGROUND INFORMATION

Biological material, such as stones, can reside at least in the kidney, ureter, or biliary duct. Stones can be extremely painful and require medical treatment. Removal of stones from the body has been accomplished by two methods in the past. The first method is stone removal through conventional surgery; a treatment with obvious disadvantages, risks and drawbacks. The second method is to remove stones under the guidance of an endoscope. In this method a grasping device is guided through the body tract to the site of the stone and is used to grasp and remove the stone under endoscopic guidance. Grasping devices which have been used in the past for the removal of stones include basket devices that have generally straight legs that bow outward from the center of the basket.

SUMMARY OF THE INVENTION

The invention provides a device and method for retrieval of material from a body. More particularly, the invention relates to a device and method for immobilizing a stone in the body with a basket of the device so the stone can be effectively fragmented and then allowing the stone and/or the pieces thereof to be removed via the basket which is formed, pursuant to the invention, of multiple, spiral-shaped, generally parallel, non-overlapping, and non-intersecting legs that are flexible and relatively closely spaced to each other (e.g., no more than about 2 mm apart).

The retrieval device of the invention includes the basket, a sheath movable relative to the basket, and a handle. The basket has spiral-shaped legs disposed around a central axis. The spiral-shaped legs have improved flexibility and moveability. In an intermediate section of the basket, the spiral-shaped legs are disposed substantially parallel to one another around the central axis. The legs do not intersect. Intersecting legs tend to restrain basket leg flexibility.

In one aspect, the invention relates to a device for retrieving material from a body. The device includes a sheath having a lumen extending therethrough and having a distal end. The device also includes a basket movable relative to the sheath from a retracted position in which the basket is withdrawn within the lumen of the sheath and an expanded position in which the basket is extended beyond the distal end of the sheath and open. The basket comprises a first portion and a second portion with two or more legs extending from the first portion to the second portion. The basket further comprises an intermediate portion between the first and second portions in which the legs are, when the basket is expanded, spirally arranged, substantially parallel, and non-intersecting. The intermediate portion of the basket is displaced radially outward relative to the first and second portions when the basket is in the expanded position. When in the expanded position, the basket can provide a support surface for the material when it is being fragmented, and it can further be used to capture the fragmented material.

Embodiments of this aspect of the invention can include the following features. For example, in one embodiment the legs of the intermediate portion of the basket may be spaced about 0.0787 inches to 0.394 inches apart. In another embodiment, an elongate member may extend within the lumen of the sheath and may be operably attached to the basket such that movement of the elongate member relative to the sheath results in the basket moving between the expanded and retracted positions.

In another aspect, the invention features a method for fragmenting and retrieving material (e.g., a stone) from a body tract This method involves inserting into a body tract a device such as the device described above. The method further includes immobilizing material in the body tract by moving the basket from the retracted position to the expanded position whereby the material is blocked, and then fragmenting the material in the body tract while using the expanded basket to limit movement of the material during fragmentation. The expanded basket can then be manipulated to capture at least some of the fragmented material within the basket. The captured fragmented material is then recovered from the body by withdrawing the device from the body tract

BRIEF DESCRIPTION OF THE DRAWINGS

FIG. 6 illustrates one embodiment of the present invention wherein the expandable element is formed by embedding material in a sheath.

FIG. 7 illustrates another embodiment of an expandable device according to the present invention.

FIGS. 8A, 8B, 8C and 8D illustrate another embodiment of an expandable device according to the present invention in which the expanded diameter of the expandable element is variable.

FIG. 9A illustrates another embodiment of the present invention in which the expandable element is formed in a guide wire with detachable proximal handles.

FIGS. 9B and 9C illustrate another embodiment of the present invention in the form of a guidewire.

FIGS. 11A and 11B illustrate another embodiment which is a variation of the embodiment shown in FIGS. 8A–8D.

FIGS. 12A–E illustrate the clinical application of the embodiment of the invention illustrated in FIGS. 11A and 11B.

FIGS. 13A–B illustrate another embodiment of the invention including the basket with spiral-shaped legs.

DESCRIPTION

Figure 1:
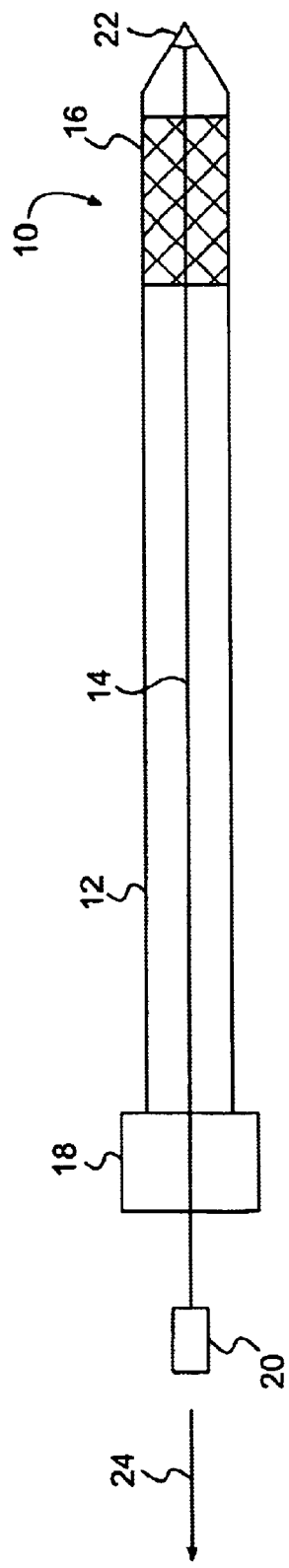
FIG. 1 is a side view of an expandable device according to the present invention.

FIG. 1 illustrates an expandable device 10 according to the present invention. In the embodiment shown in FIG. 1, expandable device 10 includes a sheath or catheter 12, cannula 14 and mesh portion 16. Catheter 12 preferably hasp at its proximal end, a handle 18. Cannula 14 is also provided, at its proximal end, with a handle 20.

Catheter 12 is preferably made of commonly available mat which provide sufficient strength and springiness for adequate operation, but which are soft enough to avoid substantial trauma or irritation to the tract or duct in which catheter 12 is deployed. Materials which may commonly be used to form catheter 12 include polyethylene, nylons, Pebax, Teflon, urethanes, silicones, and other suitable polymer materials. The material is preferably biocompatable and inert to body fluids.

In the preferred embodiment, cannula 14 is a stainless steel tube or may simply be a solid wire or a coil which extends the entire length of catheter 12 and is connected to the interior of a distal tip 22. Cannula 14 is axially movable within the lumen of catheter 12.

Mesh portion 16, in the preferred embodiment, is simply an expandable element which allows fluid flow therethrough and is preferably formed of a deformable mesh or net material, or of braided or woven fibers or metal wires, but can also be formed of a plurality of spirally arranged wires or fibers. The material is preferably formed of polymer fibers, such as nylon. In the embodiment in which mesh portion 16 is formed of a polymer mesh or netting material, the mesh size is preferably very small, and the holes in the meshing are on the order of several thousandths of an inch. It has been found that such a relatively tight mesh allows the passage of fluid therethrough, but does not allow any substantial particulate passage therethrough. In one preferred embodiment, a mesh net is formed wherein each strand of the mesh net is approximately 0.005 inches in diameter and the foramina in the net are several thousandths of an inch (e.g., 0.001 to 0.010 inches) across.

In the embodiment in which mesh portion 16 is formed of metal wires, the wires preferably comprise 0.006 inch diameter stainless steel wires. There are preferably at least three wires worked into overlapping spiral patterns. This is shown and discussed in greater detail with respect to FIGS. 5B and 5C.

Mesh portion 16 is expandable in a radial direction by manipulating cannula 14 relative to catheter 12. For instance, if cannula 14 is partially withdrawn from catheter 12 in the direction indicated by arrow 24, tip 22 is drawn closer to sheath 12 thereby exerting a compressive force on mesh portion 16. This causes mesh portion 16 to bulge outwardly in the radial direction The further tip portion 22 is brought toward sheath 12, the greater is the radial outward displacement of mesh portion 16.

Figure 2:
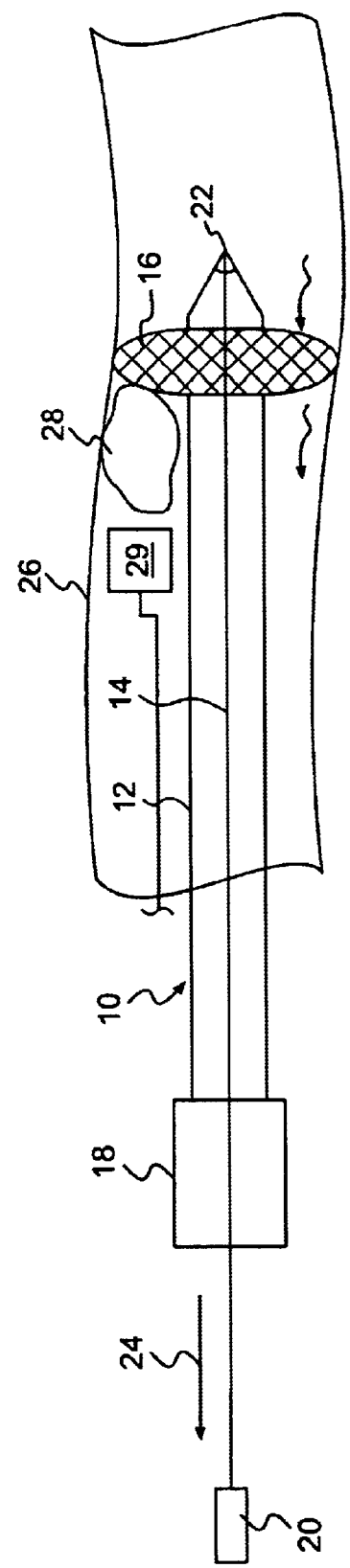
FIG. 2 is a side view of the expandable device of FIG. 1 deployed in a duct or tract or vessel of a body.

FIG. 2 illustrates expandable device 10 deployed in a duct or tract 26 of a body. Similar items are similarly numbered to those shown in FIG. 1. FIG. 2 also shows an object, such as a kidney stone or a gall stone 28, which resides in tract 26. In order to remove stone 28, expandable device 10 is used.

Expandable device 10 is first introduced (such as through a proper scope) into the duct in the retracted profile position shown in FIG. 1. After mesh portion 16 has been advanced to a desired point, preferably beyond stone 28, and preferably under endoscopic observation or guidance, handle 20 of cannula 14 is withdrawn from catheter 12 in the direction indicated by arrow 24. This causes tip 22 to move toward sheath 12 and thereby exert a compressive force or mesh portion 16. Mesh portion 16 bulges radially outwardly. Handle 20 is withdrawn from catheter 12 until the diameter of mesh portion 16 reaches a desired dimension. Typically, this dimension roughly corresponds to the lumen dimension of tract 26 so the outer periphery of mesh portion 16 contacts the inner periphery of tract 26. Mesh portion 16 thus provides a backstop, or immobilization surface, for stone 28.

After being so deployed, another instrument, such as a ballistic jack hammer-type instrument, a laser, or other treatment device 29, is inserted closely adjacent stone 28 and is used to break stone 28 into fragments. Mesh portion 16 provides a relatively rigid backstop so that a large amount of the force imparted on stone 28 is absorbed by stone 28 and is actually used in breaking stone 28, rather than being dissipated in the backstop material. It should also be noted that mesh portion 16, when in the expanded position shown in FIG. 2, provides a substantially disk-shaped object supporting surface which is used to support stone 28. This leaves the vast majority of the surface of stone 28 accessible by the instrument being used to break stone 28.

Once stone 28 is broken into pieces or fragments, those fragments are removed in any number of suitable ways. For instance baskets can be deployed to remove the fragments. However, expandable device 10 is also usefull in removing the fragments, or in sweeping the tract 26. Once stone 28 is broken into fragments, mesh portion 16 is preferably maintained in the expanded position and expandable device 10 is withdrawn from tract 26. Since mesh portion 16 is formed of a mesh size which allows fluid flow therethrough, but which does not allow any substantial particulate flow therethrough, this has the effect of sweeping tract 26 substantially clean of stone fragments.

Mesh portion 16 can also be formed to assume a substantially predetermined configuration upon being expanded. For example, the fibers in a woven mesh or net can be woven such that, when the compressive force is exerted on mesh portion 16 by sheath 12 and tip 22, the resultant expansion yields a predetermined configuration. Further, where mesh portion 16 is formed of heat-settable or other suitable polymer materials, those materials can be heat-set or thermoset so that they obtain a predetermined configuration upon expansion.

Figure 3:
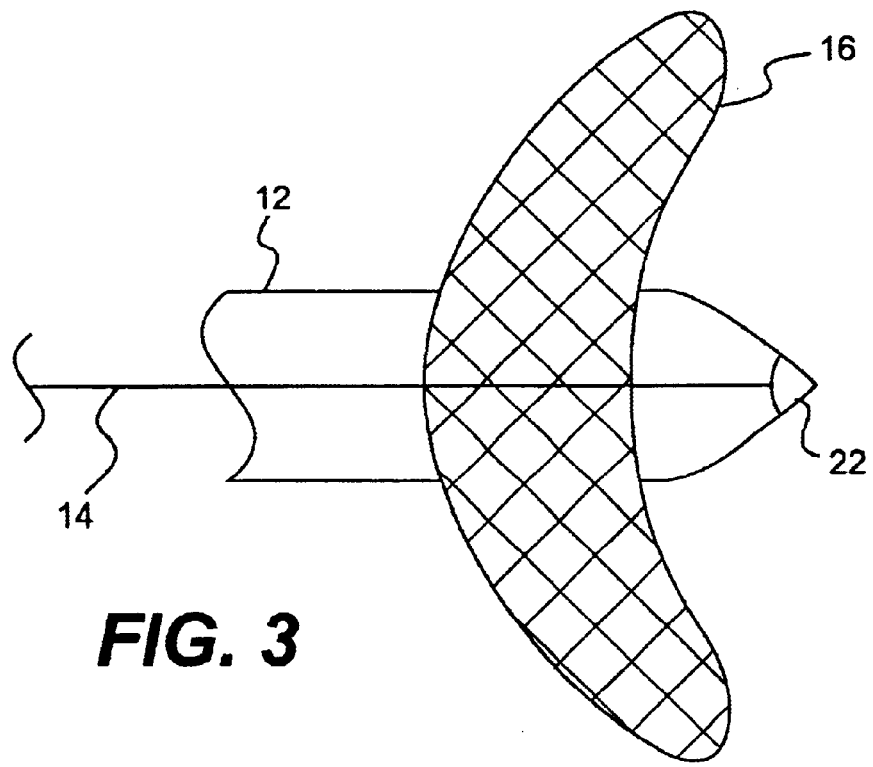
FIGS. 3 and 4 illustrate different configurations obtainable using the expandable device according to the present invention.
Figure 4:
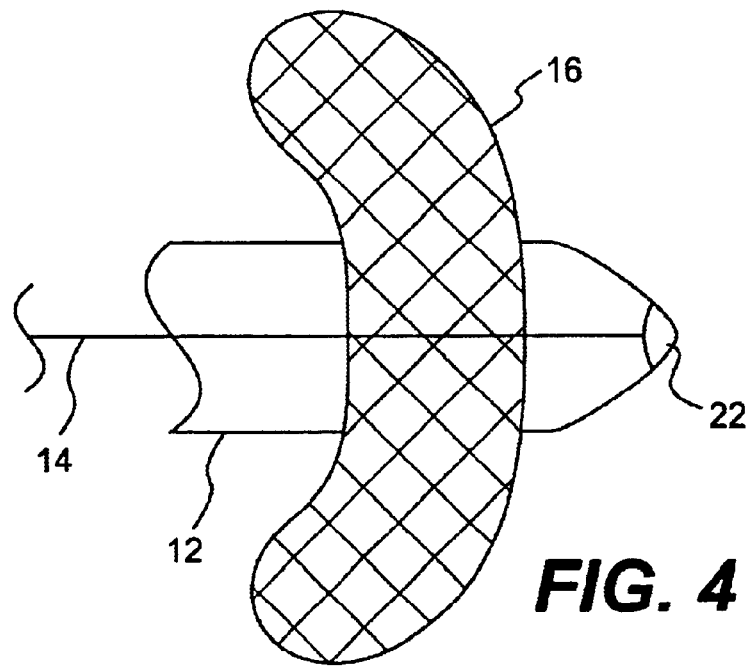

FIGS. 3 and 4 illustrate two preferred predetermined configurations. In FIG. 3, mesh portion 16 is expanded to assume a substantially concave configuration relative to tip 22. This, in some instances, is beneficial or advantageous such as when expandable device 10 is used to sweep or filter a duct or tract 26. FIG. 4 illustrates that mesh portion 16 assumes a substantially convex shape relative to tip 22. This is beneficial when expandable device 10 is used in removing stones from a duct or tract 26. For instance, in certain instances, stones can become impacted in the side tissue of a duct or tract 26. In such an instance, the shape of mesh portion 16 shown in FIG. 4 is useful in scraping or digging the stones out of the tissue defining the duct or tract. It should be noted, however, that in both FIG. 3 and FIG. 4, the shape assumed by mesh portion 16 is only a fairly shallow dish or bowl shape. This allows mesh portion 16 to provide a stone supporting or immobilization surface which still allows a great deal of access to the surface of stone 28. Therefore, if a device is introduced to break stone 28, access to stone 28 is substantially uninhibited by mesh portion 16.

Figure 5A:
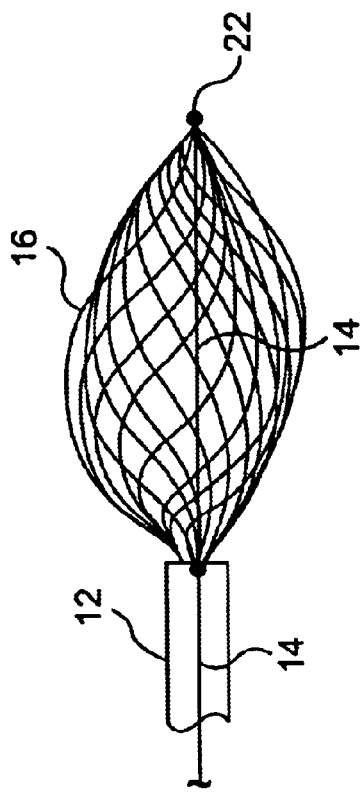
FIG. 5A shows an end view of the expandable device according to the present invention.

FIG. 5A illustrates an end view of mesh portion 16 when deployed in its expanded position. FIG. 5A shows that the preferred configuration of mesh portion 16 is substantially circular, or is a shape which is suitable to substantially conform to the interior of the duct or tract 26 in which mesh portion 16 is being deployed.

Figure 5B:
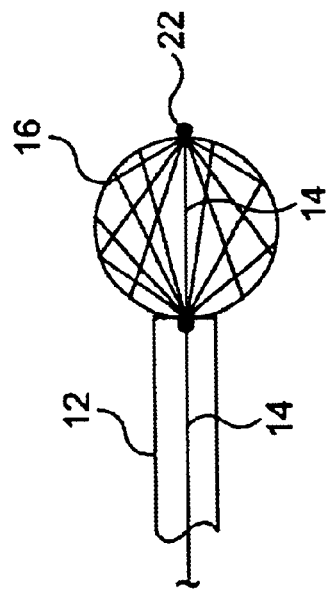
FIGS. 5B and 5C illustrate another embodiment of the present invention.
Figure 5C:
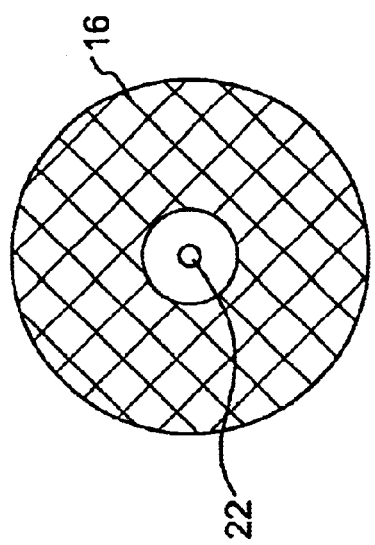

FIG. 5B illustrates mesh portion 16 formed of a plurality of spirally arranged wires or fibers. FIG. 5C illustrates the shape of mesh portion 16 in the expanded position.

Figure 5D:
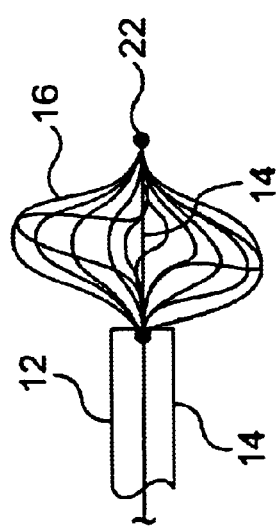
FIGS. 5D–5H illustrate other embodiments of the present invention.
Figure 5F:
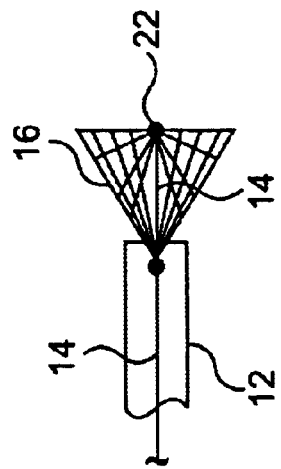
Figure 5H:
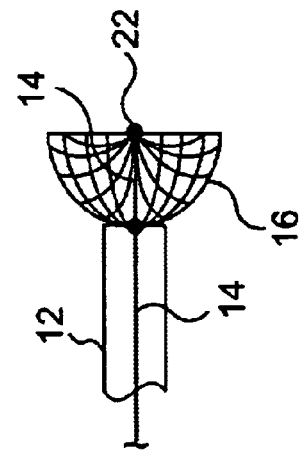
Figure 5E:
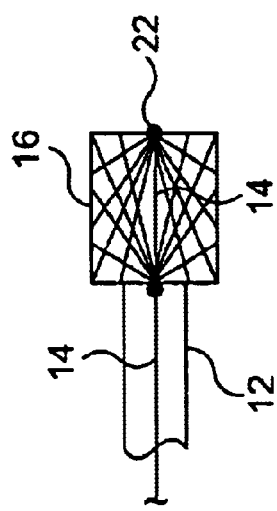
Figure 5G:
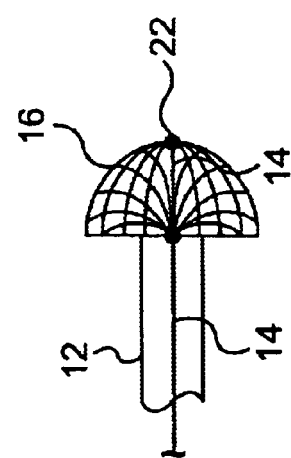

FIGS. 5D, 5E, 5F, 5G and 5H also show alternative predetermined shapes for mesh portion 16 in the expanded position. FIG. 5D shows a generally spherical shape. FIG. 5E shows a substantially square or rectangular box shape and FIG. 5F shows a pyramid or cone shape which can have a substantially square or curved base cross-section. FIGS. 5G and 5H show a hemispherical shape directed toward, and away from, lip 22. All of these shapes of mesh portion 16 can have concave or convex surfaces, as desired, and can be made of mesh netting, woven or braided fibers or wires, or any other suitable materials. Any other suitable shapes can also be used.

FIG. 6 is a cross-sectional view of another embodiment of expandable device 10. In some applications of expandable device 10, the outer diameter of expandable device 10 is crucial. In such applications, it is advantageous to provide mesh portion 16 embedded within the material defining catheter 12. When using this embodiment, no separate means are required to attach mesh portion 16 to the outer or inner surface of sheath 12. Therefore, any radial dimension which is added by such Attachment means is eliminated.

FIG. 6 shows that mesh portion 16 is formed of a mesh material which runs substantially the entire length of catheter 12 and is embedded therein. This can be accomplished by a multiple-extrusion process in which an inner first layer of the material forming catheter 12 is extruded, mesh material forming mesh portion 16 is disposed on the first extrusion, and then a second extrusion of material forming catheter 12 is performed to cover mesh portion 16 in all areas except where it is desired that mesh portion 16 be radially expandable. It should also be noted, however, that mesh portion 16 can be embedded in the material forming catheter 12 by simply taking a shorter length of mesh portion 16 and melting it into the wail of catheter 12.

In other applications, mesh portion 16 is simply secured to sheath 12 using commonly known bonding methods for metals and plastics such as ultrasonic welding or adhesives.

FIG. 7 shows another embodiment of expandable device 10 according to the present invention. In FIG. 7, expandable device 10 is provided with two mesh portions 16A and 16B. Each of mesh portions 16A and 16B is formed substantially the same as mesh portion 16 described with respect to FIGS. 1–6. However, mesh portions 16A and 16B are separated by a spacer 30. In the preferred embodiment, spacer 30 is formed of the same material as catheter 12 and is simply a generally tubular member disposed between mesh portions 16A and 16B. In such an embodiment, retraction of cannula 14 relative to catheter 12 causes a compressive force to be exerted both on mesh portion 16A and mesh portion 16B, through spacer 30. This causes both mesh portions 16A and 16B to expand radially outwardly. In the embodiment shown in FIG. 7, mesh portions 16A and 16B, when expanded, provide generally opposing object support surfaces which are shown capturing or supporting a stone 28 therebetween. Of course, any appropriate expanded configuration can be obtained with mesh portions 16A and 16B. Further, two wires such as cannula 14 can be provided to accomplish independent expansion of mesh portions 16A and 16B. While FIG. 7 shows mesh portions 16A and 16B simply trapping and holding stone 28' it should be noted that it is still possible to place an end effectuating device closely adjacent one of the mesh portions 16A and 16B to treat stone 28 through the mesh portion.

FIGS. 8A–8D illustrate yet another embodiment of the present invention. In FIGS. 8A–8D, expandable device 10 is disposed within a movable outer catheter sheath 32. Outer sheath 32 preferably extends for a major portion of the length of expandable device 10 and is axially slidable along the outer periphery of expandable device 10. Outer sheath 32 is preferably formed of a material similar to sheath 12 and has, disposed at its proximal end, a handle 34. However, outer sheath 32 may be only a relatively short sheath (on the order of the axial length of mesh portion 16) having its axial movement controlled by other means (other than handle 34) such as a control wire or a coil. Sheath 32 can be manipulated relative to expandable device 10 to obtain a desired, and controlled, radial expansion of mesh portion 16.

In the embodiment shown in FIG. 8A, mesh portion 16 has an overall axial length L1. When outer sheath 32 is placed so that its distal end 36 is coterminus with the distal end of catheter 12 (as shown in FIG. 8A) the entire length L1 of—mesh portion 16 is available for expansion. Therefore, when cannula 14 is withdrawn relative to catheter 12, and when tip 22 and the distal end of catheter 12 exert a compressive force on mesh portion 16, mesh portion 16 is free to expand throughout its entire length. This results in an expanded configuration, such as that shown in FIG. 8B, which has a diameter d1.

However, where it is desired that the diameter of the expanded portion be reduced, outer sheath 32 is moved axially relative to expandable device 10 to cover a portion of mesh portion 16. This is shown in FIG. 8C. Therefore, with outer sheath 32 deployed as shown in FIG. 8C, a smaller part of mesh portion 16 (having length L2) is available for radial, expansion. When cannula 14 is withdrawn relative to catheter 12 to cause mesh portion 16 to expand, the expanded configuration obtained by mesh portion 16 has a diameter d2 (shown in FIG. 8D) which is smaller than the diameter d1 (shown in FIG. 8B), of course, the diameter of the expanded configuration of mesh portion 16 can be continuously varied simply by varying the degree to which outer sheath 32 overlaps, and thereby constrains the expansion of, mesh portion 16. Sheath 32 could also be located distally of mesh portion 16 and pulled over mesh portion 16, and pushed to expose mesh portion 16.

FIGS. 9A–9C show yet another preferred embodiment of the present invention. In the embodiment shown in FIG. 9A, expandable device 40 is formed, in large part, as a conventional guide wire. Expandable device 40 includes an outer sheath 42 (which is often a coil) and an inner core 44 which is coupled at a distal tip 45 to outer coil 42. As with conventional guide wires, inner core 44 is movable relative to outer coil 42. However, unlike conventional guide wires, outer coil 42 is also provided with mesh or expandable portion 46. In the embodiment shown in FIG. 9A, mesh portion 46 is formed of braided fibers or wires or of mesh netting material. In another preferred embodiment shown in FIGS. 9B and 9C, mesh portion 46 can simply be comprised of straightened or substantially linear wires which, when inner core 44 is withdrawn relative to coil 42, bulge outwardly to form an object supporting surface for supporting an object (such as a stone) in a body tract. FIG. 9C shows an end view of the mesh portion 46 of FIG. 9B in the expanded position.

For expandable device 40 to operate both as a guide wire, and as an expandable device, the proximal end 48 of expandable device 40 is provided with removable handles 50 and 52. Handle 50 is preferably a snap-on handle which can be releasably secured about the outer periphery of outer coil 42. In addition, handle 52 is preferably a handle which can be releasably secured about the outer periphery of inner core 44.

The present invention will preferably be formed with one of any number of outer diameters, but will most commonly have an outer diameter of 1.5 French to 10 French. In addition, the total length of the mesh portion will have any suitable dimension, but is preferably approximately 1—3 cm in length.

While it has been disclosed that the mesh portion of the present invention is expanded to immobilize stones or objects to prevent migration of those objects during various therapies, the present invention can also be used to manipulate or remove such objects. However, immobilization is typically used during pneumatic, mechanical, electrical hydraulic, laser, or other forms of treatment of the stone. Further, it should be noted that the wires or fibers forming mesh portion 16 can have any suitable crosssection, such as flat wires, round wires or whatever is deemed appropriate. Since a low profile device is preferred in some applications, mesh portion 16 will be formed using as few wire crossovers (if any) as practicable in such applications, while still Maintaining desired stiffness for an adequate backstop.

Further, the present invention can be implemented in a multi-lumen catheter which can be used to deliver fluids, such as contrast fluid, saline-flushing fluid or caustic fluid which helps to break down the stone.

Figure 10A:
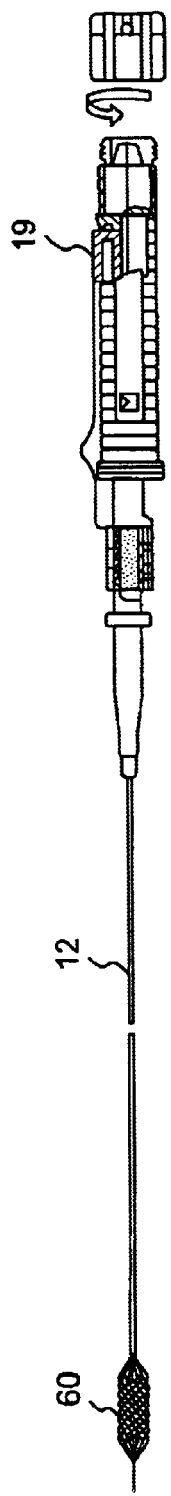
FIGS. 10A and 10B illustrate another embodiment which is similar to that of FIGS. 5B and 5C.
Figure 10B:
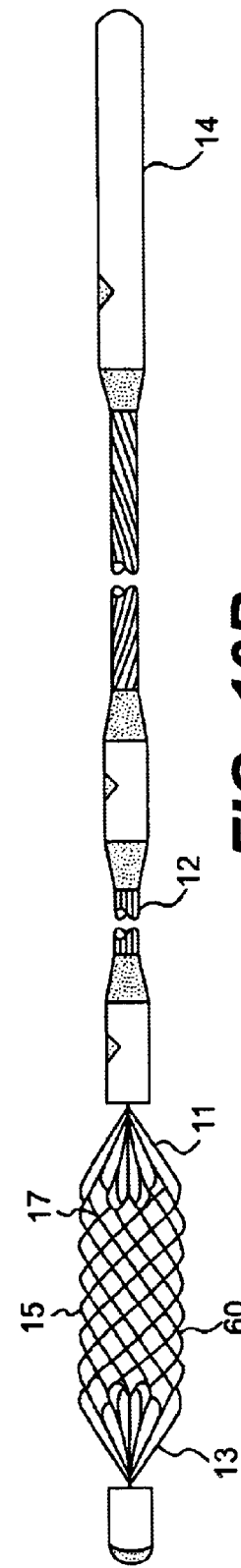

In another aspect of the invention, referring to FIGS. 10A–B, an expandable retrieval device 10 comprises a sheath 12, a basket 60, a cannula 14, and a handle 20. The basket 60 has a first basket portion 11, a second basket portion 13, and an intermediate basket portion 15 interposed between the first basket portion 11 and second basket portion 13, as also shown in FIGS. 11A and 11B. The basket 60 can be placed in a radially-expanded position, as shown in FIGS. 10A, 10B, 11B, and 13B and a retracted position, as shown in FIGS. 11A and 13A.

Figure 10C:
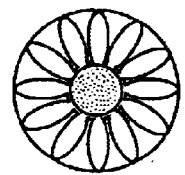
FIG. 10C is an end-view of the basket in FIG. 10B.

As illustrated in FIG. 10B, the basket 60 is comprised of multiple spiral-shaped parallel legs 17 disposed around a central axis of the basket in the intermediate portion 15. The legs 17 are non-intersecting. The legs 17 begin forming the basket 60 at the first portion 11 and end at the second portion 13. In the disclosed embodiment, the legs 17 are twelve wires that extend within the cannula 14. Other members of legs are possible such as 3, 4, 5, 6, etc. In general, the basket 60 has two or more legs, and preferably three or more. The basket legs may be made from stainless steel, nitinol or plastics. As shown in FIG. 10C, an end-view of the basket 60 comprises a star configuration.

In the disclosed embodiment, each of the parallel spiral-shaped legs in the intermediate portion of the basket 60 is spaced about 0.05 inches to 0.394 inches apart from the nearest legs, preferably 0.0787 inches apart In another embodiment, the parallel spiral-shaped legs are distanced about 0.118 inches to 0.236 inches apart, preferably 0.118 inches.

In one embodiment, the basket 60 is embedded in the wall of the sheath 12 as shown in FIGS. 11A and 11B. The cannula 14 is operably attached to the second basket portion 13. For example, the cannula may be attached to the tip 22 of the basket 60.

As shown in FIG. 11A, when the tip 22 of the basket 60 is axially-moved by withdrawing cannula 14 in the direction of the arrow, the second basket portion 13 is drawn closer to the sheath thereby exerting a compressive force on the basket 60 moving the basket between a retracted position to an expanded position shown in FIG. 11B. When the basket is compressed against the end 34 of sheath 12, the intermediate section 15 is displaced radially outward relative to the first 11 and second 13 portions when the basket 60 is in the expanded position (FIG. 11B). The further the tip 22 is brought toward the sheath 12, the greater is the radial outward displacement of the intermediate portion 15 of basket 60.

The spiral legs of basket 60 can be formed to assume a substantially predetermined configuration upon being expanded. That is, the spiral legs can be pre-formed such that when the compressive force is exerted on the basket 60 between the sheath 12 and the tip 22, the resultant expansion of basket 60 yields a predetermined configuration. The preferred configuration of the basket 60 is shown in FIG. 10B. Further, the spiral legs 17 can be formed of heat-settable or other suitable polymer materials, and those materials can be heat-set or thermoset so that the spiral legs 17 obtain the predetermined configuration upon expansion. Each of the spiral legs 17 of the basket 60 alternatively and preferably can be made of wire of rectangular cross-section, round wire, or other material (e.g., plastic) with these or other cross-sectional shapes.

FIGS. 12A–12E illustrate an application of the basket 60 of FIGS. 11A and 11B in a clinical situation. FIG. 12A shows a stone 28, such as a kidney or gall stone, located in a tract 26. An operator (e.g., a physician), preferably under endoscopic guidance, advances the sheath 12 with basket 60 in its retracted position into the tract 26 until the basket 60 is advanced preferably beyond the stone 28. Once the basket 60 is positioned beyond the stone 28, as shown in FIG. 12B, the tip 22 of the basket 60 is withdrawn by moving the cannula 14 in the direction of the arrow shown in FIG. 12B. The spiral legs 17 of the intermediate portion 15 of basket 60 expand radially as the intermediate basket portion is compressed between the sheath 12 and second basket portion 13 and the basket is moved between a retracted position and an expanded position. The cannula 14 is withdrawn until the diameter of the radially expanded intermediate portion 15 reaches a desired dimension. The radially-expanded spiral legs 17 of the basket 60 serve as an obstruction to advancement of the stone 28. The stone 28 can now be fragmented by intervention therapy such as by lithotripsy. The basket 60 in its expanded position is then maneuvered around the stone or stone fragments 28 as illustrated in FIG. 12C. The stone or stone fragments 28 enter the basket 60 between the flexible and freely moveable spiral legs 17 as shown in FIG. 12D. The basket 60 is substantially returned to its retracted position by moving the elongate member 14 in the direction of the arrow in FIG. 12E. The stone or stone fragments 28 are entrapped in the basket 60 as shown in FIG. 12E. The operator then removes the sheath 12 and the basket 60 with entrapped stone or stone fragments 28 from the tract 26.

Still referring to FIGS. 12A–12E, the stone 28, prior to being fragmented, is typically greater than about 10 mm in diameter. Once fragmented, the pieces of the stone 28 can be about 2 mm to 10 mm in diameter, and these pieces can then enter the basket 60 between the legs 17 because the distance between the legs is about 2 mm or less and because the legs are flexible. It is an important aspect of the invention that the basket 60 acts as both a stone immobilization device and a stone retrieval device.

In the preferred embodiment shown in FIG. 13A, the expandable device 10 comprises the sheath 12, and the basket 60 is moveable within the sheath 12. In general, the basket moves relative to the sheath 12 between an expanded and retracted positions. When the basket 60 is enclosed in the sheath 12, the basket 60 is in its retracted position, and it's in its expanded position when it extend from the distal end of the sheath 12 (FIG. 13B). The first basket portion 11 is attached to the cannula 14 (e.g., a solid wire or a plurality of wires) that is longitudinally disposed in the lumen of sheath 12. When the sheath 12 is moved relative to the basket 60 in the direction of the arrow (FIG. 13B), the spiral legs 17 exit from the end of the sheath and the basket 60 expands radially, thereby moving the basket 60 from its retracted position to its expanded position.

The spiral legs 17 of basket 60 in FIGS. 13A and 13B can be formed to assume a substantially predetermined configuration upon being expanded. For example, the spiral legs 17 can be pre-formed such that when the spiral legs 17 are released from the end of the sheath 32, the resultant expansion of basket 60 yields the configuration shown in FIG. 10B. The spiral legs 17 can be formed of the materials mentioned previously.

Figure 14A:
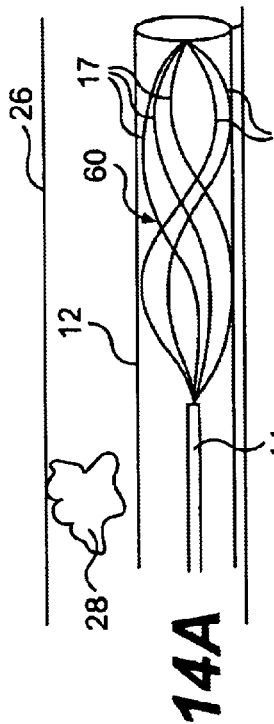
FIGS. 14A–E illustrate a clinical application of the embodiment of the invention illustrated in FIGS. 13A and 13B.
Figure 14B:
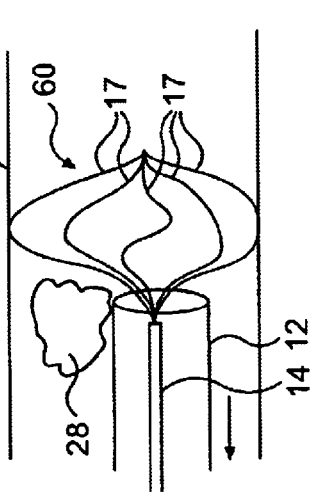
Figure 14C:
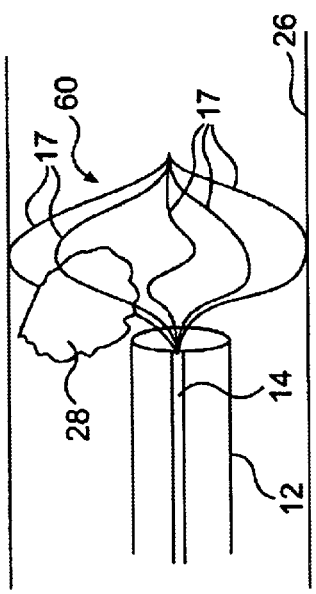
Figure 14D:
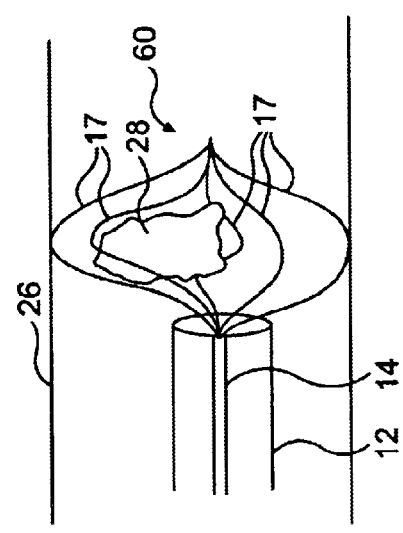
Figure 14E:
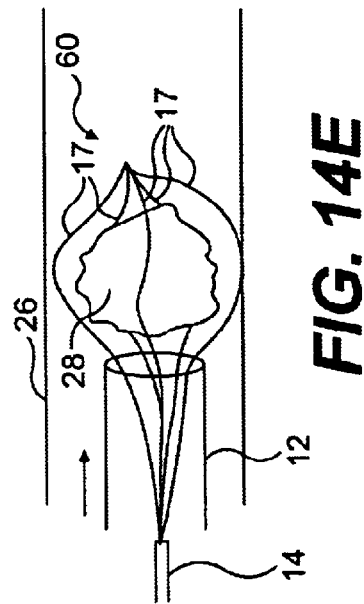

The retrieval device 10 illustrated in FIGS. 13A and 13B may be used to retrieve a stone 28, such as a kidney or gall stone, from a tract 26. FIGS. 14A–14E illustrate an application of the basket 60 of FIGS. 13A and 13B in a clinical situation. As shown in FIG. 14A, the sheath 12 with the basket 60 enclosed there within is advanced in the tract 26 until the basket 60 is advanced beyond the stone 28. When the sheath 32 is retracted in the direction of the arrow as shown in FIG. 14B, or alternatively when the cannula 14 is moved in a direction opposite to the arrow shown in FIG. 14B, the spiral legs 17 are released from the end of sheath 12 causing the basket 60 to move between a retracted position to an expanded position. In accordance with the invention, the basket 60, with its multiple, spiral-shaped, generally parallel, non-overlapping, flexible, and non-intersecting legs 17, can now be used as an immobilization device and a retrieval device. Typically, and in accordance with the invention, it will first be used as a stone immobilization device or blocking device so the stone 28 can be fragmented, and then it is used to retrieve the stone or stone fragments 28 which will tend to enter the basket 60 because of the unique shape of the legs 17. The basket 60 in the expanded position can be maneuvered around the stone fragments 28 as shown in FIG. 14C. The stone or stone fragments 28 enter the basket 60 between the flexible, freely moveable spiral legs 17 as illustrated in FIG. 14D. The sheath 12 is then moved relative to the spiral legs 17 as shown in FIG. 14E until the spiral legs 17 are snug about the stone/stone fragments 28. The operator then removes the basket 60 with the entrapped stone/stone fragments 28 and the sheath 12 from the tract 26.

In another aspect of the invention, the basket 60 shown in FIGS. 11A, 11B, 13A and 13B with multiple, spiral-shaped, generally parallel, non-overlapping, flexible and non-intersecting legs 17 can be used to retrieve intact stones having a diameter of about 0.05 inches–0.394 inches. The basket 60 in the expanded position can be maneuvered around the stone 28 as illustrated in FIG. 14C. The stone 28 enters between the flexible, spiral-shaped legs of the basket as illustrated in FIG. 14D. The sheath 12 is moved relative to the spiral legs 17 as shown in FIG. 14E until the spiral legs 17 are snug about the stone 28. The basket 60 is withdrawn from the body.

Although the present invention has been described with reference to preferred embodiments, workers skilled in the art will recognize that changes may be made in form and detail without departing from the spirit and scope of the invention.

What is claimed is:

1. A medical device, comprising:

a proximal handle;

a sheath extending from the handle to a distal end of the sheath, the sheath including a lumen extending therethrough; and a basket comprising at least three legs, said basket having a collapsed position in which the basket is collapsed within the lumen of the sheath and an expanded position in which the basket is located beyond the distal end of the sheath, the basket comprising a proximal portion comprising a length, a distal portion comprising a length, and an intermediate portion extending between the proximal and distal portions, the intermediate portion comprising a length that is greater than the length of each of said proximal portion and said distal portion, said at least three legs in the intermediate portion being spirally arranged, substantially parallel, and non-intersecting, said intermediate portion having a uniform diameter throughout its length when the basket is in the expanded position.

2. The device of claim 1 wherein the basket comprises twelve legs.

3. The device of claim 1 wherein the basket legs comprise stainless steel.

4. The device of claim 1 wherein the basket legs comprise Nitinol.

5. The device of claim 1 wherein the basket legs comprise a plastic material.

6. The device of claim 1 wherein each of the basket legs in the intermediate portion is spaced apart 0.05 inches to 0.118 inches away from the adjacent leg.

7. The device of claim 1 further comprising an elongated member extending within the lumen of the sheath and operably attached to the distal portion of the basket.

8. The device of claim 6 wherein each of the basket legs in the intermediate portion is spaced 0.0787 inches from the adjacent leg.

9. The device of claim 6 wherein each of the basket legs in the intermediate portion is spaced 0.118 inches from the adjacent leg.

10. A method for retrieving material from a body, comprising:

inserting a medical device comprising:

a proximal handle, a sheath extending from the handle to a distal end of the sheath, the sheath including a lumen extending therethrough; and a basket comprising at least three legs, said basket having a collapsed position in which the basket is collapsed within the lumen of the sheath and an expanded position in which the basket is located beyond the distal end of the sheath, the basket comprising a proximal portion comprising a length, a distal portion comprising a length, and an intermediate portion extending between the proximal and distal portions, the intermediate portion comprising a length that is greater than the length of each of said proximal portion and said distal portion, said at least three legs in the intermediate portion being spirally arranged, substantially parallel, and non-intersecting, said intermediate portion having a uniform diameter throughout its length when the basket is in the expanded position;

maneuvering the basket around said material in a body;

capturing said material in the basket; and removing the basket from the body.

11. The method of claim 10 wherein said material in a body comprises a stone.

12. The method of claim 11 wherein said stone is located in the biliary tract.

13. The method of claim 11 wherein said stone is located in the urogenital tract.

14. The method of claim 10 further comprising fragmenting the material in the body tract.

15. The method of claim 14 wherein fragmenting the material comprises laser lithotripsy.

16. The method of claim 14 wherein fragmenting the material comprises chemical lithotripsy.

17. The method of claim 10 further comprising an elongated member extending within the lumen of the sheath and operably attached at a tip of said proximal basket portion such that relative movements between the elongated member and sheath results in the basket transitioning between the collapsed position and another in which the basket is extended beyond the distal end of the sheath.

* * * * *